(12) United States Patent
Wagner et al.

(10) Patent No.: US 7,828,550 B2
(45) Date of Patent: Nov. 9, 2010

(54) ACTIVATING ENDODONTIC POINTS AND DENTAL TOOLS FOR INITIATING POLYMERIZATION OF DENTAL COMPOSITIONS

(75) Inventors: Jeff A. Wagner, Salt Lake City, UT (US); Neil T. Jessop, Sandy, UT (US); Jaleena Fischer-Jessop, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 748 days.

(21) Appl. No.: 11/232,062

(22) Filed: Sep. 21, 2005

(65) Prior Publication Data

US 2007/0065781 A1    Mar. 22, 2007

(51) Int. Cl.
*A61C 5/02* (2006.01)
(52) U.S. Cl. .................................................. 433/224
(58) Field of Classification Search ................ 433/81, 433/224, 226, 228.1, 102
See application file for complete search history.

(56) References Cited

U.S. PATENT DOCUMENTS

| | | | |
|---|---|---|---|
| 3,082,526 A | 3/1963 | Nitzche et al. | |
| 3,328,880 A | 7/1967 | Schlesinger | |
| 3,715,331 A | 2/1973 | Molnar | |
| 3,882,600 A | 5/1975 | Plymale | |
| 3,925,895 A | 12/1975 | Kliment et al. | |
| 3,926,906 A | 12/1975 | Lee, II et al. | |
| 3,959,212 A | 5/1976 | Rockett et al. | |
| 3,997,504 A | 12/1976 | Plymale | |
| 4,182,035 A | 1/1980 | Yamauchi et al. | |
| 4,240,832 A | 12/1980 | Jandourek | |
| 4,259,117 A | 3/1981 | Yamauchi et al. | |
| 4,302,381 A | 11/1981 | Omura et al. | |

(Continued)

FOREIGN PATENT DOCUMENTS

EP        0821931        2/1998

(Continued)

OTHER PUBLICATIONS

Ventura, G. et al., Morphological changes on gold-coated brass endodontic pins; Instituto di Clinica Odontoiatrica, Universitita degli Studi, Genova; Minerva Stomatol, vol. 44(6), pp. 273-283 (1995).

(Continued)

*Primary Examiner*—Cris L Rodriguez
*Assistant Examiner*—Sunil K Singh
(74) *Attorney, Agent, or Firm*—Workman Nydegger

(57) ABSTRACT

Activating endodontic points and dental tools are sized and configured to be placed in the root canal of a tooth. The activating endodontic points or dental tools are coated or impregnated with a curing agent that initiates or accelerates polymerization of a sealer or filling composition when placed in contact with the sealer or filler material. Curing agents can include amines that can destabilize a peroxide in the sealer or filler material to initiate or accelerate polymerization. Kits are also disclosed that include a plurality of endodontic points or dental tools that have different concentrations of curing agent coated on or impregnated within the endodontic points or dental tools such that the endodontic points or dental tools have different cure times. In another kit, a plurality of curing agent compositions are provided for dipping a substrate to coat or impregnate substrates having different concentrations of curing agent.

25 Claims, 5 Drawing Sheets

U.S. PATENT DOCUMENTS

| | | | |
|---|---|---|---|
| 4,425,094 A | 1/1984 | Tateosian et al. |
| 4,449,938 A | 5/1984 | Pollak |
| 4,499,251 A | 2/1985 | Omura et al. |
| 4,515,930 A | 5/1985 | Omura et al. |
| 4,525,493 A | 6/1985 | Omura et al. |
| 4,539,382 A | 9/1985 | Omura et al. |
| 4,612,384 A | 9/1986 | Omura et al. |
| 4,657,592 A | 4/1987 | Takubo |
| 4,657,941 A | 4/1987 | Blackwell et al. |
| 4,657,959 A | 4/1987 | Bryan et al. |
| 4,669,983 A | 6/1987 | Bunker |
| 4,670,576 A | 6/1987 | Bunker |
| 4,732,943 A | 3/1988 | Beech et al. |
| 4,806,381 A | 2/1989 | Engelbrecht et al. |
| 4,813,876 A | 3/1989 | Wang |
| 4,816,495 A | 3/1989 | Blackwell et al. |
| 4,872,936 A | 10/1989 | Engelbrecht |
| 4,886,843 A | 12/1989 | Walton |
| 4,966,934 A | 10/1990 | Huang et al. |
| 4,986,754 A | 1/1991 | Chang et al. |
| 5,055,497 A | 10/1991 | Okada et al. |
| 5,088,497 A | 2/1992 | Ikeda |
| 5,089,051 A | 2/1992 | Eppinger et al. |
| 5,095,045 A | 3/1992 | Winkel et al. |
| 5,108,506 A | 4/1992 | Yuhda et al. |
| 5,112,884 A | 5/1992 | Hanke |
| 5,132,458 A | 7/1992 | Honel |
| 5,177,121 A | 1/1993 | Bunker |
| 5,192,815 A | 3/1993 | Okada et al. |
| 5,192,816 A | 3/1993 | Iizuka |
| 5,236,362 A | 8/1993 | Cohen et al. |
| 5,275,562 A * | 1/1994 | McSpadden ............... 433/224 |
| 5,306,338 A | 4/1994 | Tsunekawa |
| 5,326,263 A | 7/1994 | Weissman |
| 5,338,773 A | 8/1994 | Lu et al. |
| 5,367,002 A | 11/1994 | Huang et al. |
| 5,520,725 A | 5/1996 | Kato et al. |
| RE35,264 E | 6/1996 | Bennett |
| 5,540,766 A | 7/1996 | Castellani |
| 5,548,002 A | 8/1996 | Schwabe et al. |
| 5,621,119 A | 4/1997 | Podszun et al. |
| 5,624,976 A | 4/1997 | Klee |
| 5,681,872 A | 10/1997 | Erbe |
| 5,763,622 A | 6/1998 | Podszun et al. |
| 5,859,089 A | 1/1999 | Qian |
| 5,877,232 A | 3/1999 | Storch et al. |
| 5,908,879 A | 6/1999 | Kawashima et al. |
| 5,914,356 A | 6/1999 | Erbe |
| 5,925,179 A | 7/1999 | Mannschedel |
| 5,964,592 A | 10/1999 | Hites et al. |
| 6,133,339 A | 10/2000 | Xie et al. |
| 6,183,253 B1 | 2/2001 | Billet et al. |
| 6,217,644 B1 | 4/2001 | Matsunae et al. |
| 6,224,378 B1 | 5/2001 | Valdes et al. |
| 6,353,041 B1 | 3/2002 | Qian |
| 6,371,763 B1 | 4/2002 | Sicurelli, Jr. et al. |
| 6,455,608 B1 | 9/2002 | Jia et al. |
| 6,472,454 B1 | 10/2002 | Qian |
| 6,500,004 B2 | 12/2002 | Jensen et al. |
| 6,512,068 B1 | 1/2003 | Nakatsuka |
| 6,534,121 B1 | 3/2003 | Newton et al. |
| 6,638,069 B2 | 10/2003 | Hagenbuch et al. |
| 6,729,879 B2 * | 5/2004 | Allred et al. ............... 433/226 |
| 6,787,584 B2 | 9/2004 | Jia et al. |
| 6,986,662 B2 * | 1/2006 | Haschke ............... 433/228.1 |
| 2002/0025506 A1 | 2/2002 | Hagenbuch et al. |
| 2002/0045678 A1 | 4/2002 | Lopez et al. |
| 2002/0120033 A1 | 8/2002 | Jia et al. |
| 2002/0177100 A1 * | 11/2002 | Jensen et al. ............... 433/81 |
| 2003/0105433 A1 | 6/2003 | Ruben |
| 2003/0134933 A1 | 7/2003 | Jia et al. |
| 2003/0148247 A1 | 8/2003 | Sicurelli, Jr. et al. |
| 2003/0194682 A1 * | 10/2003 | Jensen et al. ............... 433/224 |
| 2004/0137404 A1 | 7/2004 | Koch et al. |
| 2004/0249015 A1 | 12/2004 | Jia et al. |
| 2005/0196726 A1 | 9/2005 | Fischer |

FOREIGN PATENT DOCUMENTS

| | | |
|---|---|---|
| EP | 1375619 | 1/2004 |
| JP | 60-45510 | 3/1985 |
| JP | 61-151104 | 7/1986 |
| JP | 61-176506 | 8/1986 |
| JP | 63-162769 | 7/1988 |
| JP | 70-82115 | 3/1995 |
| JP | 80-99811 | 4/1996 |
| JP | 90-25208 | 1/1997 |

OTHER PUBLICATIONS

Chana, H. et al., Degradation of a silver point in association with endodontic infection; Int. Endod J., vol. 31(2), pp. 141-146 (1998).

Musikant, B.L. et al., Simplified obturation of tapered canal preparations; Compend. Contin. Educ. Dent., vol. 19(11), pp. 1152-1155 (1998).

Musikant, B.L. et al., Report of a simplified endodontic technique; Compend. Contin. Educ. Dent., vol. 20(11), pp. 1088-1090, 1092-1094 (1999).

Seidman, D., A general dentist's viewpoint of two new endodontic techniques; Compend. Contin. Educ. Dent., vol. 20(10), pp. 921-924,926,928 passim; quiz 934 (1999).

Musikant, B.L. et al., The evolution of instrumentation and obturation leading to a simplified approach; Compend. Contin. Educ. Dent., vol. 21(11), pp. 980-986, 988, 990 (2000).

Office action dated Mar. 20, 2008 cited in related U.S. Appl. No. 11/109,424.

Office action dated Mar. 8, 2007 cited in related U.S. Appl. No. 10/843,654.

Notice of Allowance dated Sep. 25, 2007 cited in related U.S. Appl. No. 10/843,654.

Office Action dated Aug. 26, 2008 in U.S. Appl. No. 11/109,424.

* cited by examiner

ACTIVATING ENDODONTIC POINTS AND DENTAL TOOLS FOR INITIATING POLYMERIZATION OF DENTAL COMPOSITIONS

BACKGROUND OF THE INVENTION

1. The Field of the Invention

The present invention relates to compositions for dental sealer and filler compositions. In particular, the present invention relates to endodontic points and dental tools that are coated or impregnated with a chemical initiator for initiating curing of a sealer or filler composition in a root canal.

2. The Related Technology

In an endodontic root canal procedure, the root canal is typically cleaned using special root canal tools and irrigation devices. Following such a root canal procedure, it is important to fill and seal the evacuated root canal to preserve the dead tooth from further decay that might compromise the integrity of the tooth and cause infection. In a typical procedure, one or more soft, resilient, needle-like inserts known as "gutta percha" points are inserted in each root canal branch to at least partially seal and fill the root canal.

The term "gutta percha" refers to a rubbery material derived from natural rubber and typically blended with zinc oxide. This particular rubbery material is preferred because it is compressible, flexible and relatively soft so that it can be used to fill voids within the exposed root canal. The gutta percha points are typically impregnated with other materials such as radiopaque solids, zinc oxide, for its medicinal properties, and other passive or active ingredients as desired.

Filling a root canal with gutta percha often requires inserting more than one gutta percha point or cone. Most root canals are narrow at the apical end and widen as they move up through the tooth. The first gutta percha point or cone is used to seal the apex and is often referred to as the master cone. Following placement of the master cone, additional gutta percha points can be added to fill the increasingly larger void of the root canal.

Experience has shown that it is impossible to completely seal a root canal using gutta percha alone. To further seal the root canal, flowable materials, such as sealing resins, are inserted into the root canal along with the gutta percha points. Due to the high viscosity of typical sealing resins, sealing resins are usually applied to the gutta percha and then inserted into the root canal or inserted using a lentalo applicator.

One feature of most sealing resins is the need to harden or cure the resin. The sealing resin remains in a liquid state until polymerized by an initiator or curing agent. The curing agent is typically mixed with the resin just prior to inserting the resin in the root canal, thereby giving the practitioner the greatest amount of time to work before the resin hardens.

One disadvantage of curable resins is that once the curing begins the reaction cannot be easily stopped or inhibited. Thus, a practitioner has only a limited time to work with the material once hardening begins. This limited time frame often results in the hardening step taking either an undesirably long amount of time or rushing the practitioner. This inability to modify cure times during a root canal procedure can make certain steps of a root canal procedure difficult or impossible. For example, a practitioner may not have sufficient time to take an X-ray to determine whether the sealing material has successfully filled the entire root canal, including lateral canals and/or whether the gutta percha points have been properly positioned. Alternatively, the curing process may take too much time, thus wasting the patient's and the practitioner's time or making it necessary for the patient to return for a follow up procedure after the resin has fully hardened.

Therefore, what is needed is a device or system that can reliably seal a root canal and give the practitioner flexibility to increase or decrease the time the practitioner has to work with a resin in the root canal during a root canal procedure.

BRIEF SUMMARY OF THE INVENTION

The present invention overcomes the above mentioned problems in the prior art by providing methods, kits, and activating endodontic points or dental tools that allow a practitioner to control the timing of the curing of an endodontic sealer or filler composition. In an exemplary embodiment, the endodontic point or dental tool includes a substrate that is sized and configured for at least partial placement into a root canal of a tooth. A curing agent is coated on or impregnated within the substrate, thereby forming an activating endodontic point or dental tool. When the activating endodontic point or dental tool is placed in contact with a sealer or filler material in a root canal, the endodontic point or dental tool initiates or accelerates polymerization of the sealer or filling material.

The curing agent can be any one of a number of components used to cure sealer or filler compositions. In an exemplary embodiment, the curing agent is an amine that initiates or accelerates polymerization of the sealer or filling composition by destabilizing a peroxide contained within the sealer or filler composition. The destabilized peroxide can then initiate free radical polymerization (e.g., of an acrylate- or methacrylate-based sealer of filler composition). Other polymerizable sealer or filler compositions that can be initiated using activating endodontic points or dental tools according to the invention include epoxy- or cationic-based compositions.

The present invention also includes methods for performing an endodontic procedure. The methods of the present invention include performing a root canal on the tooth of a person or animal to prepare the root canal for a sealer or filling composition, placing a sealer or filler composition in the root canal, and initiating or accelerating the polymerization of the filler or sealer composition by placing an activating endodontic point or dental tool in contact with the sealer of filler composition.

The activating endodontic points or dental tools can be included in a kit that provides endodontic points or dental tools with different cure times. In a first embodiment, the kit includes a plurality of substrates sized and configured for at least partial placement into a root canal of a person, and each substrate has a curing agent coated on or impregnated within the substrate such that the curing agent is capable of initiating or accelerating polymerization of an endodontic sealer or filling material when placed in contact with it. The concentration of the curing agent can vary between different substrates in the kit such that different substrates can provide different curing times.

A kit containing one or more master cones and one or more accessory cones can be used to select when or how fast to initiate the curing process. According to one embodiment, the master cone may be treated with a curing agent to initiate either slow or fast curing. Accessory cones designed to be placed into a root canal after the master cone can be treated with a curing agent. In the case where the master cone is treated to initiate slower curing one or more accessory cones can be used to initiate faster curing. In some cases only the accessory cones will be treated such that the master cone does not itself initiate curing.

In another embodiment, a kit according to the present invention includes a plurality of substrates sized and configured for at least partial placement into a root canal of a person and a plurality of different curing agent compositions. The curing agent compositions comprise a carrier and a curing agent for coating or impregnating the plurality of substrates. Each of the plurality of different curing agent compositions has a different concentration of curing agent such that the different curing agent compositions cause different curing times when the substrate coated therewith is placed in contact with a filling or sealing material.

The present invention provides significant advantages to dental practitioners performing an endodontic procedure. The methods, kits, and activating endodontic points or dental tools of the present invention allow a practitioner to better control when a sealer or filler composition is cured during the endodontic procedure and how long the curing takes. Using the present invention, a practitioner can prepare and place a curable sealer or filling material in the root canal and wait for a desired amount of time before initiating or causing complete polymerization. The practitioner can control the timing of curing by selecting when to place the activating endodontic point or dental tool in the sealer or filler material. Furthermore, by controlling the concentration of the curing agent on or within the endodontic point or dental tool, the rate of polymerization can also be controlled.

Moreover, the present invention allows a sealer or filler material to be cured throughout and within the sealer or filler material. Unlike light curing alone, which may only cure the upper portion of the sealer or filler material, the present invention allows rapid curing along the entire root canal.

Providing the practitioner with control over timing and duration of curing reduces the time and expense of an endodontic procedure and can improve the quality of the procedure. One advantage of controlling cure timing is that the practitioner can choose to perform a step such as taking X-rays to determine proper placement of the filler or sealer material and/or endodontic point (e.g., a master cone). Because the practitioner can wait to cause curing of the sealer or filler material, the practitioner can cause very rapid curing after the practitioner has performed any necessary work. This allows subsequent procedures, such as restorative procedures, to be performed immediately following the sealing or filling procedure. For example, this feature can allow a patient to receive a root canal and a restorative post procedure in a single office visit.

These and other advantages and features of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The invention includes endodontic points and dental instruments that are used to control curing of sealer and filler compositions in a root canal procedure. The endodontic points or dental tools comprise a substrate that is coated or impregnated with a curing agent to form an activating endodontic point or dental instrument. When contacted with a sealer or filler composition, the curing agent initiates or accelerates polymerization of the sealer or filler. During an endodontic procedure, timing the curing of the endodontic filler or sealer composition can be easily controlled by the practitioner by selecting when to immerse the activating endodontic point or dental tool. Furthermore, the cure time can be further controlled by controlling the amount of curing agent that is coated on or impregnated within the substrate.

II. Activating Endodontic Points and Dental Instruments

A. Substrate

Figure 1:
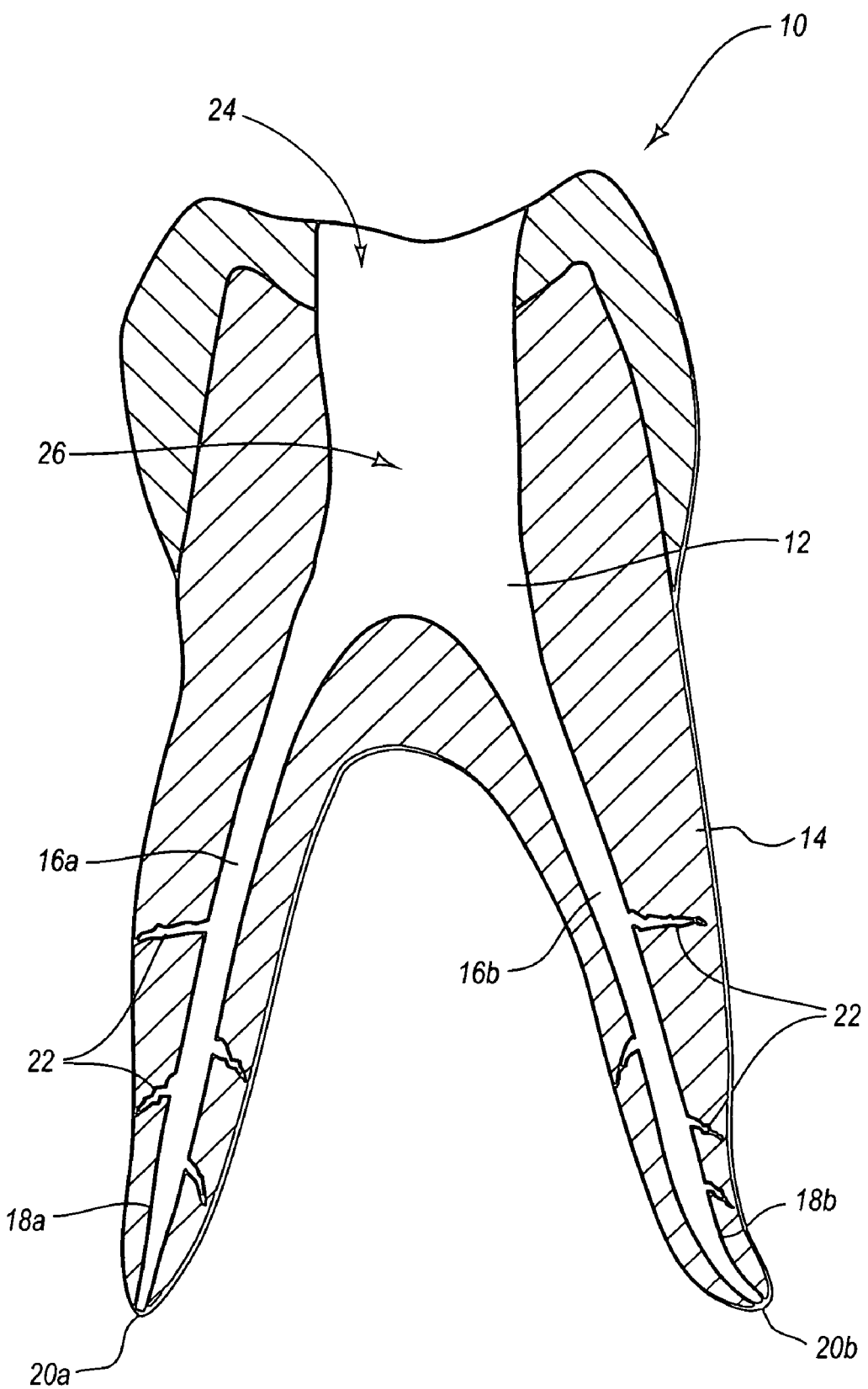
FIG. 1 illustrates an exemplary tooth with its root prepared in an endodontic procedure for sealing and filling according to an exemplary embodiment of the present invention.

In a preferred embodiment, the activating substrate of the present invention is an endodontic point. However, almost any material that can be sized and configured for insertion into a root canal of a person can be used as the substrate for the present invention. FIG. 1 depicts a tooth 10 that has been subjected to a root canal procedure such that a substrate can be inserted therein. The tooth 10 includes a root canal 12 in tooth root 14. Root canal 12 includes root canal portions 16a and 16b. Root canal portions 16a and 16b terminate at apexes 18a and 18b, respectively to create root openings 20a and 20b. Lateral canals 22 extend into root 14 from root canal 12. An opening 24 in the crown of the tooth provides access to root canal 12.

The substrate of the present invention is sized and configured to be inserted through opening 24 and into root canal 12. In one embodiment, the substrate is configured to be inserted into the pulp chamber 26. Alternatively, the substrate of the present invention can be sized and configured to be at least partially placed in the root canal portions 16a or 16b.

Typically, substrates that can be inserted into root canal 12 have a diameter between about 0.1 and 1.1 mm for human teeth. Animals however, can have much larger root canals, such as up to about 20 mm.

Figure 2:
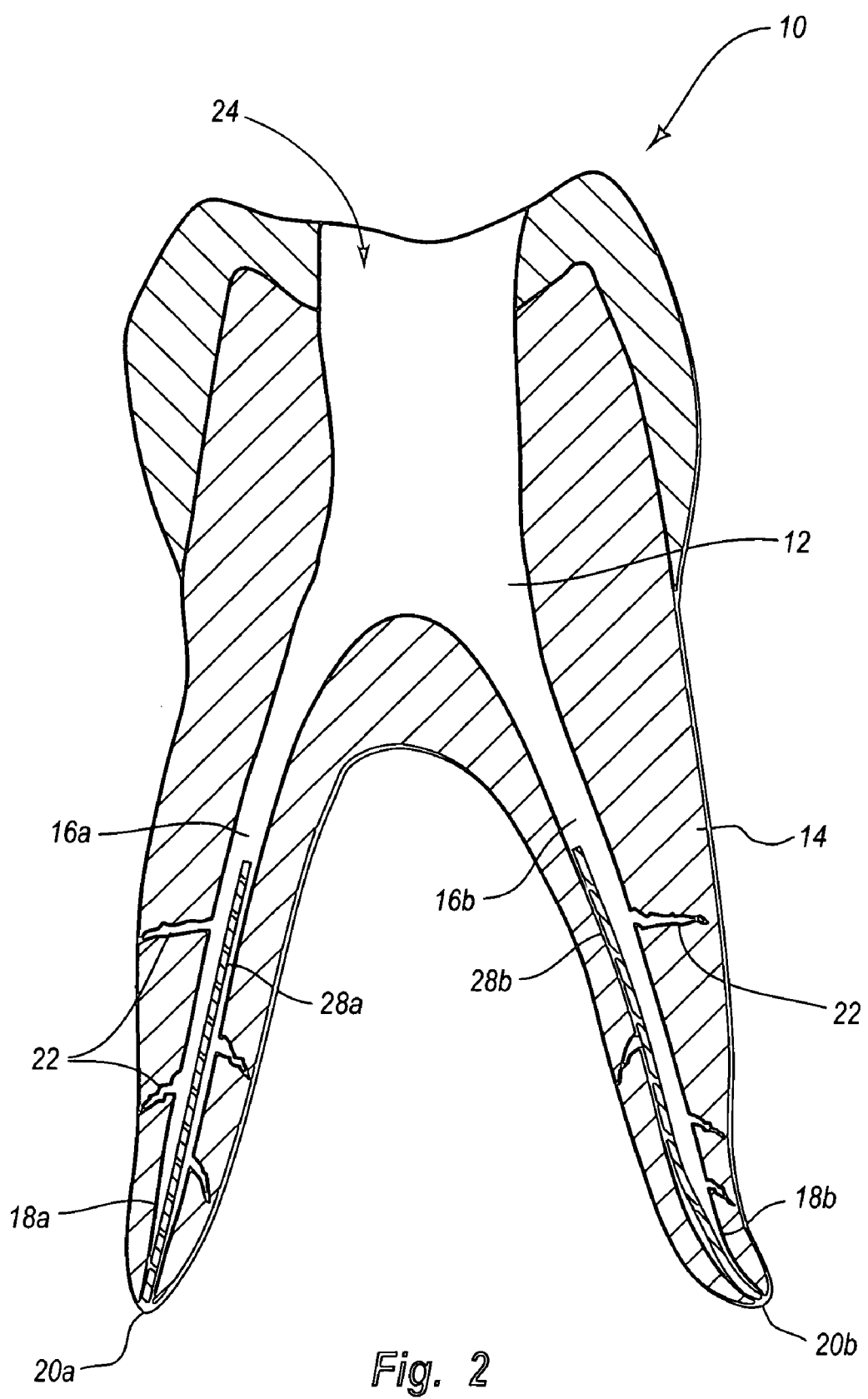
FIG. 2 illustrates placement of an endodontic point in the apex of the tooth of FIG. 1.

In an exemplary embodiment, the substrate of the present invention is an endodontic point. FIG. 2 shows endodontic points 28a and 28b inserted into apexes 18a and 18b respectively. As discussed below, endodontic points 28a and 28b can be coated or impregnated with a curing agent according to the present invention. Endodontic points 28a and 28b can be made of gutta percha and are used for their typical benefit, which is to plug or seal root openings 20a and 20b in root canals 16a and 16b respectively.

Using endodontic points 28a and 28b as a substrate according to the present invention has the added benefit of not requiring additional materials or tools to be placed in the root canal. This aspect of the invention can be particularly beneficial where the substrate needs to be placed near apex 18 since root canal 16a and 16b can be very narrow at the apex.

Figure 5:
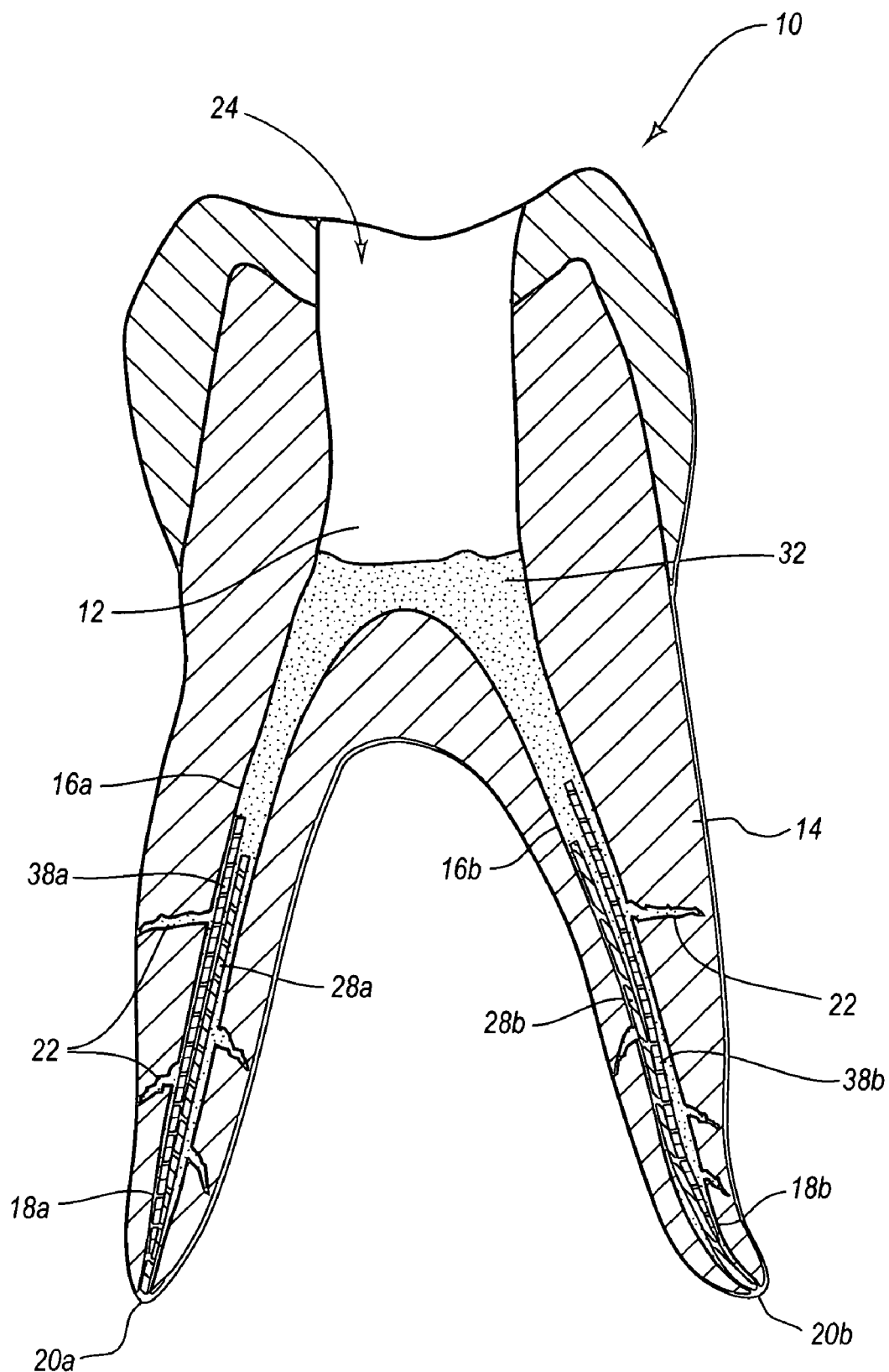
FIG. 5 shows the tooth and filler or sealer composition of FIG. 4 with a pair of activating, accessory endodontic points placed in the sealer or filler composition to initiate or accelerate curing.

Endodontic points 28a and 28b shown in FIG. 2 are master points and can be used as a substrate according to the present invention. However, as shown in FIG. 5, accessory cones such as endodontic points 38a and 38b can also be used as a substrate. In existing endodontic procedures, accessory cones are typically used to seal lateral canals 22, where the master cones are used to plug the opening in the apex. In the case where accessory cones are used, only the accessory cones are activating so that curing is not initiated or accelerated until placement of the accessory cones. This allows a dentist or endodontist to take one or more X-rays to ensure proper placement of the filler or sealer and the master cone(s) prior to initiating or accelerating curing. It is also within the scope of the invention to use a master cone that is treated to initiate either fast or slow curing.

In an alternative embodiment, a dental tool or other device can be used as a substrate. For example, syringe 30, shown in FIG. 3 (e.g., an outer surface of cannula 34), can be used as a substrate in addition to being used as a tool to inject a sealer composition into the root canal. Alternatively, the substrate can be another dental tool such as an endodontic file or thin piece of plastic or other material so long as the substrate is sized and configured to be placed into at least a portion of a root canal.

B. Sealer and Filler Compositions

The sealing and filling compositions used with the activating endodontic points and dental tools according to the present invention include at least one polymerizable resin material. The polymerizable resin is initially in a liquid or shapeable form. As discussed below, the curing system causes polymerization of the resin to form a polymerized and hardened material.

Figure 3:
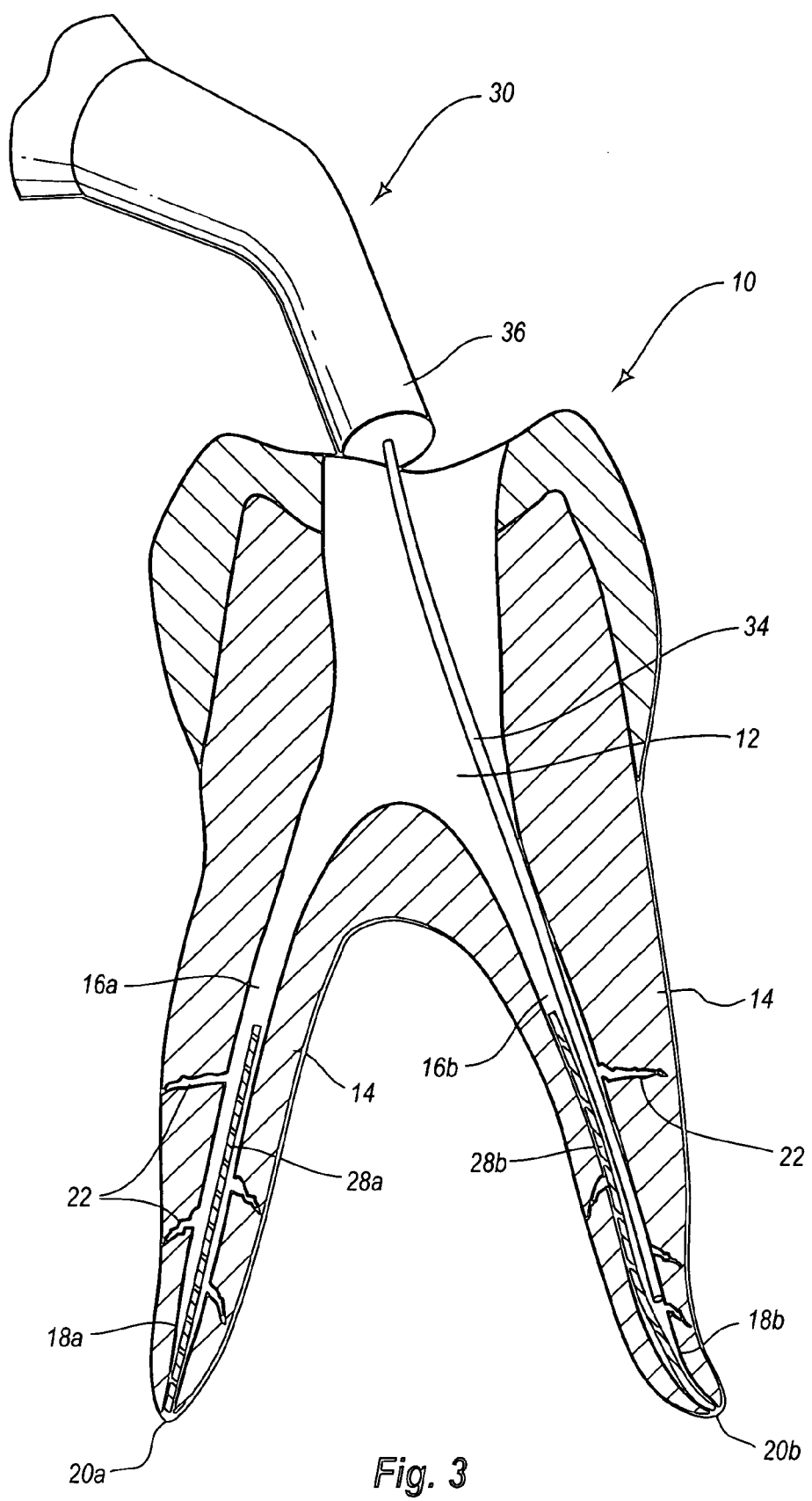
FIG. 3 illustrates filling the root canal of the tooth of FIG. 2 with an endodontic sealer or filler composition.
Figure 4:
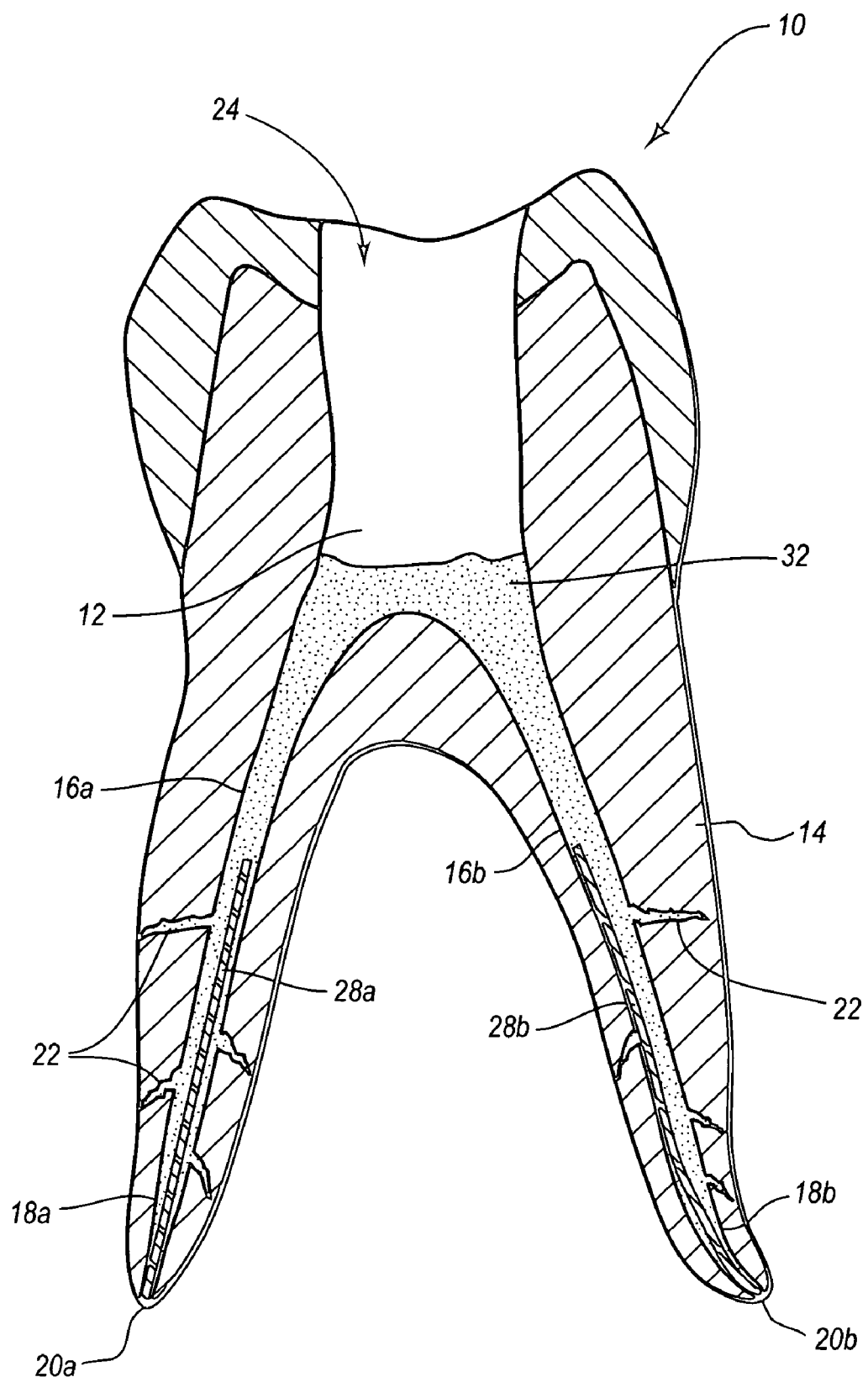
FIG. 4 Illustrates the tooth of FIG. 2 partially filled with a sealer or filler composition.

As shown in FIGS. 3 and 4, sealer or filler composition 32 is placed in root canals 16a and 16b. Sealer or filler composition 32 fills root canals 16 such that root canals 16 and lateral canals 22 are sealed off from each other and opening 24. Sealing root canals 16 and lateral canals 22 help prevents bacteria and other microbes from entering root canal 12 or lateral canals 22 and spreading infection or decay within tooth root 14.

Any polymerizable material capable of sealing a root canal can be used with the present invention. Examples of suitable primary polymerizable resins include a wide range of acrylates, methacrylates, alkylhydroxy methacrylates, alkylamino methacrylates, exopy-based compositions, cationic-based compositions, and derivatives thereof. More specific examples of polymerizable materials include glycidyl dimethacrylate, 2-hydroxy ethyl methacrylate, 3-hydroxy propyl methacrylate, 4-hydroxy butyl methacrylate, triethylene glycol dimethacrylate, and polyethylene glycol dimethacrylate. An example of an epoxy-based endodontic sealant resin that can be catalyzed using catalyzing endodontic points or tools according to the invention is AH 26, available from Dentsply.

In one exemplary embodiment, the polymerizable resin includes an oxyphosphorus alkyl methacrylate, such as bis glycerol dimethacrylate phosphate. Examples of other oxyphosphorus alkyl methacrylates within the scope of the invention include bis 2-hydroxy ethyl methacrylate phosphate, phosphate ester of p-hydroxyphenyl methacrylamide, phosphate ester of 3-hydroxy propyl methacrylate, and z phosphate ester of 4-hydroxy butyl methacrylate. The oxyphosphorus group increases the adhesiveness and water solubility (i.e. hydrophilicity) of the resulting resin.

One or more additional (or diluent) monomers can be added to achieve the desired properties of initial flowability, curability, and final cured strength and hardness. Diluent monomer suitable for use in the present invention include urethane dimethacrylate, p-hydroxyphenyl methacrylamide, butane diol dimethacrylate, and bisphenol-A-diglycidyl dimethacrylate ("Bis-GMA").

The primary polymerizable resins are preferably included in a concentration ranging from about 1% to about 90% by weight of the composition, more preferably from about 10% to about 80% by weight, and most preferably from about 20% to about 70% by weight of the composition.

The diluent monomers may be included in amounts of up to about 95% by weight of the composition, preferably in a range from about 10% to about 80%, and more preferably in a range from about 30% to about 70% by weight of the composition.

C. Curing Agents

The curing agent is selected to initiate or accelerate polymerization of the sealer or filler composition. The curing agent may be one part of a curing system that is capable of polymerizing the endodontic sealer or filler composition. Generally, any component of a curing system can be used as the curing agent so long as that compound can initiate polymerization of the sealer or filler composition. The curing agent may be selected to initiate curing of any polymerizable sealant or filler composition, including but not limited to, acrylate- and/or methacrylate-based compositions, epoxy-based compositions, and cationic-based compositions.

The curing agent is typically coated on or impregnated within the substrate, either prior to or just before use. When the coated or impregnated substrate is placed in contact with a sealer or filler composition, the curing agent causes polymerization of the sealer or filler composition.

The sealer and filler composition within the scope of the invention can be heat curable, chemically curable, photo curable, dual curable, or use any other curing process or combination of curing processes that require the addition of a chemical component in the curing process.

The curing agent of the present invention can be an initiator or it can be an additive that works with an initiator to initiate or accelerate polymerization of the sealer or filler composition. Initiators are compounds that induce polymerization of the polymerizable material. Initiators include radiant energy polymerization initiators or chemical initiators with an appropriate additive, such as an organic amine additive.

Examples of photoinitiators within the scope of the invention include camphor quinone, benzoin methyl ether, 2-hydroxy-2-methyl-1-phenyl-1-propanone, diphenyl 2,4,6-trimethylbenzoyl phosphine oxide, benzoin ethyl ether, benzophenone, 9,10-anthraquinone, and derivatives thereof.

Photoinitiators are preferably included in an amount in a range from about 0.05% to about 5% by weight of the composition, more preferably in a range from about 0.1% to about 2% by weight, and most preferably in a range from about 0.2% to about 1% by weight of the composition. In the case of a photocurable sealer or filling composition, the polymerizable resin is advantageously stable in the presence of the photoinitiator absent the application of radiant energy.

In the case of chemical and dual curable sealer or filling compositions the curing system is typically provided in two or more parts that are mixed to initiate curing. One part of the system includes constituents of the resin sealer or filling together with one-half of the chemical cure system (e.g., a peroxide compound), while another part includes constituents of the resin sealing with the other half of the chemical cure system (e.g., an amino compound).

Examples of chemical initiators include a wide range of peroxides, other per components, and other free radical generators. A two-part chemical curing system as described more fully below, typically includes a peroxide constituent in one part and an amino compound in another. Exemplary peroxides include benzoyl peroxide, 2-butanone peroxide, lauroyl peroxide and tert-butyl peroxide. Examples of amino compounds include dimethylamino ethyl methacrylate, triethyl amine, 2-dimethylamino ethanol, diethylamino ethyl methacrylate, trihexyl amine, N,N-dimethyl-p-toluidine (also referred to as DNPT), N-methylethanolamine, 2,2'(p-tolyimino) diethanol (also referred to as TIDE), and derivatives thereof.

In an exemplary embodiment, the curing agent applied to the substrate is an amine or other compound that can destabilize a peroxide compound. The peroxide compound is included in the resin and the amine compound, which is coated or impregnated on the substrate, initiates or accelerates polymerization when it comes into contact with the peroxide in the filler or sealing composition.

D. Method of Making Activating Endodontic Points and Dental Tools

In an exemplary embodiment, the activating endodontic points and dental tools are made by dipping the substrate into a composition that includes the curing agent. In one embodiment, the curing agent is mixed with a polymer or a solvent and the substrate is dipped into the polymer or solvent. By mixing the curing agent with a polymer or solvent, the polymer or solvent can be used as a carrier for coating or impregnating the substrate. In another embodiment, the substrate is dipped directly into a pure solution of curing agent.

While any coating or impregnation method can be used to apply the curing agent to the substrate, using a carrier can be particularly effective. First, using a carrier can provide an appropriate distribution of the curing agent over the substrate. For example, where a dental tool such as a metal tool is being used, a polymeric mixture can be used that has a viscous or adhesive property that causes the polymeric mixture to adhere to the dental tool. In an another embodiment, where a gutta percha point is used, a solvent can be used that can penetrate the gutta percha and impregnate it. Nevertheless, dental tools can be coated with a solvent and gutta percha endodontic points can be coated with a polymeric material.

A second advantage of using a carrier such as a solvent or polymer to deliver the curing agent is that mixing the curing agent allows the concentration of the curing agent to be controlled. Typically, the cure time depends on the concentration of the curing agent in the sealer or filler composition. This is accomplished by making the curing agent the limiting reagent or choosing a curing agent that can accelerate the reaction. In one exemplary embodiment, the curing agent is an amine that destabilizes a peroxide in the sealer or filler material. The concentration of the amine in the sealer or filler material determines in large part the magnitude of the cure time.

Coating or impregnating the substrate by dipping the substrate directly in a curing agent such as TIDE or DNPT results in cure times of less than about 30 seconds. By mixing the curing agent with a carrier such as a polymer or a solvent, the cure time can be extended to any desired amount of time.

Suitable polymers useful as a carrier for the curing agent include acrylate based polymers such as methacrylates and di-acrylates. In an exemplary embodiment, the polymers used as a carrier for the curing agent are similar or identical to the polymers used in the sealer or filling material. A solvent is typically used to impregnate an endodontic point or dental tool. An example of a solvent suitable for using in the present invention is toluene.

In an exemplary embodiment, the curing agent is an amine that is included in a polymeric material and the concentration of amine is between about 0.1 and about 35% of the polymeric mixture. The concentration of curing agent will depend on the curing agent selected. For example, TIDE is typically used in a range of between about 5% and 35%, and more preferably in a range of about 20%-25% of the coating. A coating having TIDE in a concentration of about 20% to about 25% causes the sealer or filler material in the root canal to cure in about 2-4 minutes.

In another example, DNPT is used with the solvent toluene, preferably in a concentration of about 0.1% to about 20%, and more preferably in a concentration of about 1%-2%. DNPT in a concentration of about 2% in toluene and impregnated on an endodontic point causes curing in about 8 minutes when placed in a sealer or filler in a root canal.

Those skilled in the art will recognize that there are many combinations of initiators, peroxides, amines, and other compounds that work with many different curable resins and that these different compounds can be used as a curing agents to carry out the invention described herein. Those skilled in the art are also familiar with cure times for various concentrations of curing agent in curable resins. Thus, while various examples have been provided for purposes of illustrating the invention, those skilled in the art can easily adapt these teachings to numerous curable resins and curing systems that are available for sealing or filling root canals.

The carrier compounds described above, including polymers and solvents are examples of carrier compound means for coating or impregnating a substrate with a curing agent.

When making an activating endodontic point or dental tool according to the present invention, any portion of the substrate can be coated or impregnated. Typically, for an endodontic point, the entire length of the point is coated or impregnated since gutta percha points may be completely inserted into the root canal. A dental tool on the other hand is typically only partially inserted into the root canal. Thus, only a portion of the dental tool is typically coated or impregnated so as to not waste the active agent.

The activating endodontic points and dental tools of the present invention can be coated or impregnated during manufacture. Alternatively, a curing agent composition can be provided to the dental practitioner who then mixes and/or dips a substrate in the curing agent composition to prepare the activating endodontic point or dental tool just before use.

In yet another embodiment of the present invention, a plurality of activating endodontic points or dental tools are provided to the dental practitioner. In this embodiment, the plurality of activating endodontic points and/or dental tools can have different concentrations of the curing agents and are included in a kit. The endodontic points or dental tools have different concentrations of curing agent that correspond to different cure times. During an endodontic procedure, the dental practitioner can select an activating endodontic point or dental tool that provides the proper cure time for that particular procedure.

In yet an alternative embodiment, the kit can include a plurality of curing agent compositions that have varying amounts or concentrations of curing agent. In this embodiment, a dental practitioner dips the substrate into the curing agent composition just prior to use. The dental practitioner can control the cure time by selecting the proper curing agent composition.

III. Methods of Using Activating Endodontic Points and Dental Tools to Control the Cure Time of an Endodontic Filler or Sealer The endodontic points and dental tools of the present invention can be advantageously used in an endodontic procedure to control the cure times of the endodontic sealer or filler composition. FIGS. 1-4 illustrate a tooth in various steps of an endodontic procedure.

A. Methods for Sealing or Filling a Root Canal

As discussed above, FIG. 1 shows tooth 10 with root canal 12 that has been prepared using known endodontic techniques. In FIG. 2, master endodontic points 28a and 28b are placed in root openings 20a and 20b respectively. To ensure that endodontic points or cones 28a and 28b form a reliable seal within openings 20a and 20b, a procedure involving "tug back" is preferably performed. One of ordinary skill in the art of endodontics will know when there is sufficient tug back to confirm an adequate seal of the apexes 18a and 18b by master endodontic cones 28a and 28b. Sufficient tug back indicates that the fit between the gutta percha cone and the apex is sufficiently tight to adequately seal the apex and prevent flow of sealer or filling material into the surrounding bone tissue.

In a preferred method for placing a resinous sealer or filling material within a root canal, FIG. 3 depicts syringe 30 having a narrow diameter cannula 34 attached to tip 36 of syringe 30 used to insert sealer or filling material into root canal 12. Due to the narrow opening of the cannula 34, and because typical sealer or filling materials are often viscous, it can be advantageous for syringe 30 to be attached to a high pressure hydraulic injection system. An example of high pressure hydraulic syringes or systems are set forth in U.S. Pat. No. 6,425,885, which is assigned to Ultradent, Inc. Examples of narrow cannulas sized for entry into a root canal are set forth in U.S. Pat. No. 6,079,979, which is assigned to Ultradent Products, Inc. For purposes of disclosing hydraulic pressurizing systems and cannulas sized to fit within a root canal, the foregoing patents are incorporated herein by reference.

The tip of the cannula 34 is initially placed within the root canal 12 near one of the apexes 18a or 18b and sealer or filling material 32 (FIG. 4) is injected into root canal 12. As the resinous material begins and continues to fill up the root canal portion 16b, the cannula 34 is slowly raised or withdrawn. This manner of filling the root canal 12 with resinous material minimizes or eliminates the formation of air pockets or bubbles as the resin is progressively placed within the root canal 12. This procedure greatly improves the ability of the resin to initially purge most or all of the air from within the root canal 12. As shown in FIG. 4, accessory points 38a and 38b are inserted into root canal 12 to seal the root and/or deliver sealing material 30. One or both accessory points 38a and 38b can be treated with a curing agent to initiate or accelerate curing.

In an alternative, conventional embodiment, the sealer or filler composition is placed in root canal 12 by first dipping the endodontic points in a resin and then inserting the point into the root canal. When the endodontic point is dipped, resin is coated thereon and is carried into the root canal with the endodontic point. In one embodiment, some or all of the sealer or filler composition is introduced into the root canal using a master cone. In addition, or alternatively, some or all of the sealer of filler composition can be introduced into the root canal using one or more accessory cones.

Some or all of the endodontic cones can be treated to initiate curing. In the case where the master cone is used to introduce the sealer or filler composition into the root canal, the accessory cones may be treated with a curing agent and used to initiate curing. In the case where the accessory cones are used to introduce the sealer or filler composition into the root canal, the master cone may be treated so as to initiate curing after insertion of the composition-laden accessory cone(s).

B. Controlling Cure Times Using Activating Endodontic Points or Dental Tools Controlling the curing time of an endodontic sealer or filling material according to the present invention is accomplished by either (i) selecting when to place an activating endodontic point or dental tool in the curable sealer or filling material, and/or (ii) selecting an activating endodontic point or dental tool with a predetermined amount or concentration of curing agent.

The first aspect of controlling curing according to the present invention enables a practitioner to delay curing of the sealer of filler composition by choosing when to place the activating endodontic point or dental tool in contact with the sealer or filler composition 32. In the exemplary embodiments illustrated in FIGS. 1-4, accessory endodontic points or cones 38a and 38b are used by the practitioner to control curing of the endodontic sealer or filler composition. In this embodiment, sealer or filler composition 32 contains little or no curing agent when it is placed in the root canal. In addition, the master endodontic cones 28a and 28b are not activating and therefore do not initiate or accelerate curing. Thus, the practitioner can have any amount of time to place the sealer or filler material 32. In addition, the practitioner has time to perform other desired procedures. For example, the practitioner can take X-rays of tooth 10 to determine whether the master endodontic points 28a and 28b have properly sealed the apex and/or whether the sealer or filler material has been properly placed in root canal 12 and/or lateral canals 22.

Once the practitioner has completed or performed the desired dental procedures, activating accessory endodontic points 38a and 38b are placed in root canal 12 as shown in FIG. 5. The curing agent coated on or impregnated within accessory endodontic points 38a and 38b comes into contact with the sealer or filler composition and initiates curing. Because the practitioner has already had time to perform necessary procedures, sufficient curing agent can be included such that accessory points 38a and 38b cause sealer or filling material 32 to cure very rapidly. The accessory points can be made according to any of the methods described above. For example, the accessory points can be pre-coated or impregnated during manufacture, or they can be activated just prior to use.

In an alternative embodiment, a dental tool such as syringe 30 can be used to initiate or increase curing of the sealer or filler material. For, example, during an endodontic procedure, when the practitioner desires to have the sealer or filling agent cured, the practitioner can dip a syringe cannula 34 in a curing material and then place the coated syringe in contact with the sealer or filler composition.

In yet an alternative embodiment, the activating dental tool can be an applicator that is simply a piece of plastic or other material that is made activating by applying a curing agent thereto. At least a portion of the plastic or other material is sized and configured to be placed in the root canal of a person or animal such that it can be inserted into the root canal and placed in contact with the sealer or filler composition.

In some cases, the circumstances of the procedure will determine which activating endodontic point or dental tool the practitioner will use. One advantage of a dental tool such as a piece of plastic is that it can be used at anytime without regard to its use in the dental procedure. In contrast, placement of an endodontic point is sometimes determined according to the needs of the procedure. However, using an activating endodontic point can be advantageous because the endodontic point is intended to permanently remain in the cured product.

Activating endodontic points and dental tools used in the kits and methods of the present invention can have varying concentrations of curing agent and thus provide different desired cure times. During an endodontic procedure, those skilled in the art will know how much time they will need before the sealer or filler composition hardens. The present invention provides the practitioner with the ability to select any desired curing time during the procedure. If the practitioner needs 1 minute, 10 minutes, 2 hours or any other amount of time, the practitioner can select an activating endodontic point or dental tool with a curing agent in a concentration that provides the desired cure time.

In addition to providing controlled timing, the activating endodontic points and dental tools of the present invention can provide convenience. For example, a practitioner may want to use an activating master endodontic point even though curing would begin as soon as the sealer or filler composition is placed in the root canal. In this embodiment, the practitioner can eliminate the need to mix the sealer or filler composition, thus making the endodontic procedure more convenient. Furthermore, the practitioner can be provided with a set of activating endodontic points that give the practitioner a selection of different concentrations of curing agent and thus different cure times.

The present invention is also not limited with respect to use of a single activating endodontic point or dental tool during an endodontic procedure. For example, an activating master endodontic point can be used with an activating accessory endodontic point. The master endodontic point can initiate relatively slow curing and the accessory endodontic point can be used to accelerate curing. In yet another embodiment, a master endodontic point, an accessory endodontic point, and/or a dental tool can be used to cure the sealer or filling material. Each activating point or tool can be coated and/or impregnated with the same or differing concentrations of curing agent and can be placed in contact with the same or different portions of the sealer or filling material.

The present invention also includes using more than one type of curing system. For example, a chemical curing system can be used in conjunction with a heat curing system or a light curing system. Those skilled in the art will recognize the many different combinations of curing systems that can be used with the foregoing teachings of the present invention.

The following examples provide specific formulas of exemplary embodiments of the present invention and should be considered as illustrative of the present invention and not limiting in any way.

EXAMPLE 1

Acrylate Resin Coating

In Examples 2-5, below, a curing agent is diluted in an acrylate resin coating. Diluting the curing agent in the acrylate resin gives the coating a desired cure time. The acrylate resin coating used in the formulas of examples 2-5 is prepared by first preparing a prepolymer mixture according to the following formula:

| | |
|---|---|
| Krasol LBH 2000 (linear polybutadiene polymer with hydroxyl end groups) | 80.499% |
| Dabc LBH 2000 (tin catalyst) | 0.001% |
| Desmodur W bis(4-isocynotocyclohexyl)methane | 19.500% |

The acrylate resin coating is then formed using the prepolymer according to the following formula:

| | |
|---|---|
| Prepolymer | 2.5% |
| 2-hydroxyethyl acrylate | 2.5% |
| Polyethylene glycol diacrylate | 70.8% |

The Prepolymer and the 2-hydroxyethyl acrylate are allowed to react to completion and are then directly mixed with the polyethylene glycol diacrylate to form the Acrylate Resin Coating.

Curing Agent Formulas

In each of Examples 2-5, an endodontic point was coated or impregnated with the curing agent formula and placed in an acrylate-based sealer or filler composition. The acrylate-based sealer or filler composition included benzoyl peroxide as an initiator. The amount of sealer or filler composition was similar to the amount that would occupy a typical root canal.

EXAMPLE 2

An endodontic point coated with a coating having the following formula caused the sealer or filler material to cure in about 2 minutes at 37° C.

| | |
|---|---|
| Acrylate Resin Coating | 37.5% |
| Triethylene glycol dimethacrylate | 37.0% |
| P-TIDE | 25.0% |
| Irgacure (a photoinitiator) | 0.5% |

EXAMPLE 3

An endodontic point coated with a coating having the following formula caused the sealer or filler material to cure in about 8 minutes at 37° C.

| | |
|---|---|
| Acrylate Coating | 97.5% |
| DMPT | 2.0% |
| Irgacure | 0.5% |

EXAMPLE 4

An endodontic point coated with a coating having the following formula caused the sealer or filler material to cure in about 18 minutes at 37° C.

| | |
|---|---|
| Acrylate Resin Coating | 98.0% |
| P-TIDE | 1.5% |
| Irgacure | 0.5% |

EXAMPLE 5

An endodontic point was impregnated with the following curing agent and solvent by briefly immersing the endodontic point in the solution and then allowing the solvent to volatize. The endodontic point was then placed in the sealer or filler composition, which caused curing in about 3 minutes at 37° C.

| | |
|---|---|
| Toluene | 90.0% |
| P-TIDE | 10.00% |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An activating dental implement for chemically initiating or accelerating curing of an endodontic sealer or filling material located within a root canal of a tooth, comprising:
   a substrate sized and configured for at least partial placement into a root canal; and
   an unreacted chemical curing agent coated on or impregnated within the substrate that is available for chemically initiating or accelerating curing of a chemical cure endodontic sealer or filling material located within a root canal of a tooth when the substrate is placed in contact therewith, the unreacted chemical curing agent being only a first part of a two-part chemical curing system and being devoid of a second part of the two-part chemical curing system so as to remain unreacted until contacted with the second part of the two-part chemical curing system previously placed within the root canal,
   the activating dental implement being configured so as to be insertable into a root canal of a tooth.

2. An activating dental implement as in claim 1, wherein the substrate is an endodontic point.

3. An activating dental implement as in claim 2, wherein the endodontic point is a master cone.

4. An activating dental implement as in claim 1, wherein the unreacted chemical curing agent is a destabilizing chemical compound that is the first part of a two-part chemical curing system that includes the destabilizing chemical compound and a peroxide so that the curing agent can destabilize a peroxide included in a sealer or filler composition located within a root canal.

5. An activating dental implement as in claim 4, wherein the destabilizing chemical compound comprises an amine selected from the group consisting of dimethylamino ethyl methacrylate, triethyl amine, 2-dimethylamino ethanol, diethylamino ethyl methacrylate, trihexyl amine, N,N-dimethyl-p-toluidine, N-methylethanolamine, 2,2'(p-tolyimino) diethanol, derivatives thereof, and combinations thereof, and wherein the unreacted chemical curing agent is devoid of a peroxide.

6. An activating dental implement as in claim 1, wherein the unreacted chemical curing agent is a peroxide that is the first part of a two-part chemical curing system that includes a peroxide and a destabilizer for the peroxide, the peroxide being selected from the group consisting of benzoyl peroxide, 2-butanone peroxide, lauroyl peroxide, tert-butyl peroxide, derivatives thereof, and combinations thereof, and wherein the unreacted chemical curing agent is devoid of a destabilizer for the peroxide.

7. An activating dental implement as in claim 1, wherein the unreacted chemical curing agent is a first part of an epoxy curing system selected to catalyze an epoxy- or cationic-based polymer composition that includes another part of the epoxy curing system.

8. An activating dental implement as in claim 1, further comprising carrier means for coating or impregnating the substrate with the curing agent.

9. An activating dental implement as in claim 8, wherein the carrier means comprises a polymeric material.

10. An activating dental implement as in claim 9, wherein the unreacted chemical curing agent has a concentration between about 5% to about 35% of the polymeric material.

11. An activating dental implement as in claim 9, wherein the unreacted chemical curing agent has a concentration between about 20% and about 25% of the polymeric material.

12. An activating dental implement as in claim 9, wherein the polymeric material comprises a polymer selected from the group consisting of bis glycerol dimethacrylate phosphate, bis 2-hydroxy ethyl methacrylate phosphate, phosphate ester of p-hydroxyphenyl methacrylamide, phosphate ester of 3-hydroxy propyl methacrylate, phosphate ester of 4-hydroxy butyl methacrylate, epoxy-based resins, cationic-based resins, and combinations thereof.

13. An activating dental implement as in claim 8, wherein the carrier means comprises a solvent.

14. An activating dental implement as in claim 13, wherein the curing agent has a concentration between about 0.1% and about saturation in the solvent.

15. An activating dental implement as in claim 13, wherein the solvent comprises toluene.

16. An activating endodontic point for chemically initiating or accelerating curing of an endodontic sealer or filling material located within a root canal of a tooth, comprising:
   an endodontic point substrate sized and configured for at least partial placement into a root canal; and
   an unreacted chemical curing agent that is only a first part of a two-part chemical curing system coated on or impregnated within the endodontic point substrate such that placement of the activating endodontic point in contact with an endodontic sealer or filling material that contains a second part of the two-part chemical curing system initiates or accelerates curing of the endodontic sealer or filling material,
   the activating endodontic point being configured so as to be insertable into a root canal of a tooth.

17. A kit for use in initiating or accelerating curing of an endodontic sealer or filling material located in a root canal comprising a plurality of endodontic point substrates according to claim 16.

18. A kit for use in initiating or accelerating curing of an endodontic sealer or filling material comprising one or more activating endodontic points according to claim 16 and one or more non-activating endodontic points.

19. A kit as in claim 18, wherein the one or more activating endodontic points comprise one or more master endodontic cones.

20. A kit for initiating or accelerating curing of an endodontic sealer or filling material, comprising:
   a plurality of substrates sized and configured for at least partial placement into a root canal of a tooth; and
   an unreacted chemical curing agent that is only one part of a two-part chemical curing system coated on or impregnated on two or more of the substrates, the chemical curing agent being capable of initiating or accelerating curing of an endodontic sealer or filling material that comprises another part of the two-part chemical curing system when placed in contact therewith, and wherein the concentration of the chemical curing agent coated on or impregnated within at least two of the substrates differs such that at least two of the substrates cause different curing rates relative to each other when placed in contact with an endodontic sealer or filling material.

21. A kit as in claim 20, wherein the plurality of substrates comprise endodontic points.

22. A kit for initiating or accelerating curing of an endodontic sealer or filling material, comprising:
- a plurality of substrates sized and configured for at least partial placement into a root canal of a tooth; and
- a plurality of different unreacted chemical curing compositions, each comprising a polymer carrier material and an unreacted curing agent that is only one part of a two-part chemical curing system for coating or impregnating the plurality of substrates, at least two of the plurality of different unreacted chemical curing compositions having different concentrations of the unreacted chemical curing agent such that at least two of the unreacted curing compositions cause different cure rates relative to each other when each is placed in contact with a filling or sealing material.

23. A kit as in claim 22, wherein the carrier comprises a solvent.

24. A method for initiating or accelerating curing of an endodontic sealer or filling material, comprising:
- preparing a root canal of a tooth for placement of an endodontic sealer or filler material;
- placing an endodontic sealer or filling material within the root canal, the endodontic sealer or filling material comprising a first part of a two-part chemical curing system;
- applying a second part of the two-part curing system to a substrate to form an activating dental implement, the second part of the two-part chemical curing system being applied to the substrate just prior to inserting the activating dental implement into the root canal; and
- while the endodontic sealer or filler material is still uncured or only partially cured, contacting the endodontic sealer or filling material with the activating dental implement in order for the second part of the two-part chemical curing system to initiate or accelerate curing of at least a portion of the endodontic sealer or filling material.

25. A method as in claim 24, wherein the substrate is an endodontic point.

* * * * *

UNITED STATES PATENT AND TRADEMARK OFFICE
CERTIFICATE OF CORRECTION

| | | |
|---|---|---|
| PATENT NO. | : 7,828,550 B2 | Page 1 of 1 |
| APPLICATION NO. | : 11/232062 | |
| DATED | : November 9, 2010 | |
| INVENTOR(S) | : Wagner et al. | |

It is certified that error appears in the above-identified patent and that said Letters Patent is hereby corrected as shown below:

Column 5
Line 45, change "exopy-based" to --epoxy-based--

Column 6
Line 1, change "monomer" to --monomers--

Column 8
Line 17, change "as a curing agents" to --as curing agents--

Column 9
Line 57, change "sealer of filler" to --sealer or filler--

Column 10
Line 12, change "sealer of filler" to --sealer or filler--
Line 46, change "For, example" to --For example--

Signed and Sealed this
Third Day of May, 2011

David J. Kappos
*Director of the United States Patent and Trademark Office*